United States Patent [19]

Nieh et al.

[11] 4,182,864

[45] Jan. 8, 1980

[54] TRIETHYLENEDIAMINE PROCESS

[75] Inventors: Edward C. Y. Nieh; George P. Speranza, both of Austin, Tex.

[73] Assignee: Texaco Development Corporation, White Plains, N.Y.

[21] Appl. No.: 944,538

[22] Filed: Sep. 21, 1978

[51] Int. Cl.$^2$ .......................................... C07D 295/02
[52] U.S. Cl. ..................................................... 544/352
[58] Field of Search ................................. 544/351, 352

[56] References Cited

U.S. PATENT DOCUMENTS 3,080,371  3/1963  Spielberger et al. ................. 544/352

*Primary Examiner*—Jose Tovar

*Attorney, Agent, or Firm*—Carl G. Ries; Robert A. Kulason; James L. Bailey

[57] ABSTRACT

A process is provided for recovering substantially pure triethylenediamine in liquid tertiary amine solutions directly from the crude triethylenediamine reaction mixture without resort to a need to purify the triethylenediamine by crystallization. The process includes initially admixing a tertiary amine with a crude triethylenediamine liquid reaction product mixture. The admixture thus formed is then distilled under conditions such that the triethylenediamine and tertiary amine codistill as a substantially pure triethylenediamine solute in liquid tertiary amine solution. The collected codistillate being substantially free of reaction by-products can be used directly to catalyze urethane systems.

5 Claims, No Drawings

TRIETHYLENEDIAMINE PROCESS

BACKGROUND OF THE INVENTION

1. Field of the Invention

This invention relates to the recovery of substantially pure triethylenediamine; and more particularly to a process for recovering a triethylenediamine solute in a liquid tertiary amine solution directly from a crude triethylenediamine reaction product mixture.

2. Description of the Prior Art

Triethylenediamine (TEDA) is a valuable commercial product, particularly as an accelerator or catalyst in conventional urethane systems employing a wide variety of isocyanates and polyols as reactants. Several methods for preparing triethylenediamine are well known. For example, one process is described by O. Hromatka et al. in Berichter Volume 76, pages 712–717 (1943) wherein triethylenediamine is obtained by the process of heating the dihydrochloride of N-(2-hydroxyethyl)piperazine. Another process involves the gaseous phase cyclization of N-hydroxyethylpiperazine vapor in the presence of a solid acid catalyst. Another well-known process is described in U.S. Pat. No. 3,080,371 to Spielberger et al which includes the liquid phase process of heating N-(2-hydroxyethyl)piperazine in the presence of a mono- or dicarboxylic acid catalyst at a temperature of from about 230° to about 350° C.

Generally, such well-known processes result in the formation of crude reaction product mixtures containing the triethylenediamine, water, by-product such as piperazine and high molecular weight polymers, catalyst and solvents, if any are employed. Triethylenediamine is normally distilled from the crude reaction product by fractional distillation followed by one or more crystallization steps. The substantially pure solid triethylenediamine thus recovered is then dissolved in a suitable solvent for use as a urethane catalyst.

These generally described conventional techniques for recovering triethylenediamine have several disadvantages. Pure triethylenediamine has a freezing point of 159.8° C. and a boiling point of 174° C. Pure triethylenediamine thus is normally a liquid over a very narrow temperature range of 14.2° C. In view of this fact, it is extremely difficult to separate triethylenediamine from its crude reaction product mixtures by conventional techniques other than by crystallization. For example, pure triethylenediamine cannot be readily separated from reaction mixtures by conventional distillation techniques. Further, triethylenediamine readily freezes in the distillation equipment including condensation apparatus, vent lines, and the like, causing an equipment blockage problem. Solid, e.g., crystallized triethylenediamine is also somewhat difficult to work with. For example, the crystalline material tends to hydrate. Further, the solid compound has a slight odor requiring the use of special handling equipment in some cases.

In as much as conventional urethane systems normally utilize liquid reaction components and the solid triethylenediamine is difficult to handle, store and ship, the solid is normally dissolved in a suitable solvent such as a glycol which is compatible with urethane systems. Such triethylenediamine solutions have been prepared in a number of ways. For example, a substantially pure solid triethylenediamine may be obtained by the methods previously described herein and then dissolved in a suitable solvent. Such technique has the disadvantages as just described, particularly involving the need for crystallization and for handling a solid triethylenediamine. In yet other methods, such as that described in U.S. Pat. No. 3,993,651, the solvent employed has also been used as part of a purification scheme. However, such solvent, of course, is not an active catalyst in preparing a subsequent polyurethane. Thus, such solvent must necessarily be shipped along with the active triethylenediamine catalyst ingredient which involves additional costs.

SUMMARY OF THE INVENTION

In accordance with the broader aspects of the invention, a process has been devised to purify a crude triethylenediamine reaction product mixture by resort to a solvent which itself acts as a co-catalyst in preparing conventional polyurethanes. In essence, the crude triethylenediamine is distilled in admixture with a tertiary amine which also active is a polyurethane catalyst. the resultant admixture is distilled under conditions such that the tertiary amine and the triethylenediamine form a substantially pure codistillate, which is thereafter collected as a substantially pure triethylenediamine dissolved in a tertiary amine liquid solution.

In a preferred embodiment a crude aqueous triethylenediamine liquid reaction mixture is obtained by heating N-hydroxyethylpiperazine in the presence of a carboxylic acid to a temperature ranging from about 230° to 350° C., more preferably 240°–270° C. and adding water to the crude reaction effluent obtained therefrom. Tertiary amine is then admixed with the crude aqueous mixture. The resultant admixture is fractionally distilled to provide a tertiary amine-TEDA codistillate collected at a head temperature ranging from about 135° to about 215° C. at atmospheric pressures. The codistillate is then liquified by condensation.

DETAILED DESCRIPTION OF THE PREFERRED EMBODIMENTS

According to a preferred process, substantially pure triethylenediamine (TEDA) is recovered directly from a crude aqueous triethylenediamine liquid reaction mixture as a solute in a liquid tertiary amine solution. The liquid solution can thereafter be used directly to catalyze urethane systems. In these instances, both the tertiary amine and TEDA are active catalysts in such systems yielding overall excellent activity.

Preferably the crude triethylenediamine reaction effluent is obtained by initially charging a heated reaction kettle fitted with agitation apparatus and a distillation column with N-(2-hydroxyethyl)piperazine (HEP) and a carboxylic acid catalyst. The liquid phase reaction is carried out by well known methods, for example, those disclosed in U.S. Pat. No. 3,080,371.

The crude triethylenediamine reaction effluent thus obtained is collected in an appropriate vessel with sufficient water added thereto to produce a crude aqueous liquid TEDA reactant mixture containing preferably 50–85% water. To the aqueous mixture is added a tertiary amine in an amount sufficient to provide a collected codistilled solution which contains 10–30% by weight TEDA.

In yet another embodiment the crude triethylenediamine product may be in solid form as in the wet hexahydrate crystalline form.

The admixture of tertiary amine and crude aqueous reaction product is then distilled by employing conventional distillation techniques and equipment. Preferably, the distillation is carried out continuously by employing a plurality of distillation columns, but can be carried out as, for example, a batchwise or semicontinuous process. During the distillation, the lower boiling point materials, such as water, piperazine and other by-products are initially collected by taking them overhead at the lower distillation temperatures.

The tertiary amine and triethylenediamine codistillate is collected overhead at temperature within the range of about 135° to about 215° C. at atmospheric pressure. Such distillation temperature, of course, will depend upon the particular tertiary amine employed. The codistillate faction is then collected by conventional condensation methods. This can be accomplished without encountering TEDA freezing problems.

The triethylenediamine solution thus prepared contains substantially pure triethylenediamine which is present substantially as a solute of the tertiary amine solution. The triethylenediamine solution is substantially free of reaction by-product and can be used directly to catalyze urethane systems. The triethylenediamine thus recovered is not in the crystal or solid form, thus substantially reducing the problems of handling, and shipping previously encountered. In addition, as noted above there is an added advantage in using a tertiary amine as a solute in this process in that a material of this type is normally itself a urethane catalyst, and thus materially enhances the catalytic activity of the triethyelendiamine.

Any number of tertiary amines may be used which codistill with triethylenediamine at a temperature ranging from about 135° to about 215° C. Particularly preferred tertiary amine solvents include trimethylaminoethyl piperazine, N-ethylmorpholine, N,N,dimethylethanolamine, beta, beta-dimethylaminoethyl ether, N,N-dimethylpiperazine, N-methylmorpholine, N,N-diethylethanolamine, 2-dimethylaminoethyl-3-dimethylaminopropyl ether, tri-n-propylamine, triallylamine, tetramethylethylenediamine, tetramethylpropylenediamine, and other homologues of this type containing various lower alkyl groups. Most preferred is N,N-dimethylethanolamine.

In carrying out the process of the invention, as discussed above, water is preferably added to the crude triethylenediamine effluent to produce a crude aqueous liquid triethylenediamine reaction product mixture. The addition of water is not critical to carrying out the process of the instant invention, but, is added primarily as a diluent and/or solvent. Since TEDA is soluble in water, the aqueous crude reaction product mixture is more easily handled and transferred at lower temperatures without encountering freezing or precipitation of the dissolved TEDA.

The specific amount of tertiary amine which can be added to a given crude triethylenediamine reaction product mixture is primarily dependent upon the amount of triethylenediamine present. Thus, the amount of tertiary amine required to codistill substantially all of the triethylenediamine present can be readily determined by those having ordinary skill in the art without undue experimentation.

The admixture of tertiary amine and crude triethylenediamine reaction product may then be distilled employing any well-known distillation techniques and equipment.

The process of the invention can be employed to recover substantially pure triethylenediamine solutions directly from crude triethylenediamine reaction product reaction mixtures obtained by practically any known liquid phase process for the preparation of triethylenediamine.

The codistillation step can be carried at superatmospheric or sub-atmospheric pressures, if desired. Such techniques and temperature required are well-known to those skilled in the art and can be readily determined without resort to excessive experimentation. Fractional distillation columns may be utilized with very narrow head temperature ranges to reduce, for example, the amount of piperazine present in the collected product mixture. Excess water can be removed from the admixture of tertiary amine and aqueous TEDA reaction product mixture by, for example, azeotropic distillation techniques. Such technique can include the initial addition of a lower boiling point non-deleterious hydrocarbon to the crude reaction product mixture.

The process of the instant invention may be employed to recover TEDA solutions from a crude liquified reaction product reaction of known vapor phase preparation procedures. However, most vapor phase procedures for producing triethylenediamine form by-products which have a boiling point in a range such that codistillation in accordance with the present invention may not produce a TEDA solution free of by-products. Therefore, in order to practice the instant invention, the vapor phase reaction products could require removal of the similar boiling impurities, prior to the addition of the tertiary amine.

The process of the invention is further disclosed in the following examples, which are meant to be illustrative but not limitative thereof.

EXAMPLE I

To a two liter, three necked flask equipped with a 14 inch Goodloe packed column and distillation head, thermometer and addition funnel was charged 150 grams of crude aqueous triethylenediamine. The crude material contained 77% water, 22% triethylenediamine, 0.2% hydroxyethylpiperazine and traces of other materials such as piperazine. The crude triethylenediamine reaction product mixture employed was prepared substantially by the process of heating N-(2-hydroxyethyl)-piperazine in the presence of a catalytically effective amount of an aromatic carboxylic acid at a temperature of about 245° to about 260° C.

After taking the bulk of the water, 1062 grams overhead by distillation, dimethylaminoethanol in an amount of 400 grams was added to the pot. The remaining water was removed together with 85 grams of dimethylaminoethanol as an intermediate fraction. The main fraction, 1384 grams, was then collected at a 150° to 155° C. overhead temperature, while an additional 750 grams of dimethylaminoethanol was fed to the pot at a rate that kept the pot temperature from rising above 168° C. Distillation was terminated when the addition of the above-mentioned dimethylaminoethanol was completed. The main overhead product consisting of 22% triethylenediamine and 78% of dimethylaminoethanol was found to be a desirable urethane catalyst. The bottoms product, consisting of 23.5% triethylenediamine and 75% of dimethylaminoethanol may be recycled to the next batch distillation.

EXAMPLES II-V

By procedures similar to Example I, from crude 30% aqueous TEDA in an amount of 500 grams and several tertiary amines as listed below in an amount of 450 grams purified solutions of TEDA were obtained in the corresponding tertiary amines. The TEDA-tertiary amine solutions were homogeneous at or above 50° C. In some instances, when cooled to room temperature the TEDA crystallized out making it necessary to adjust amounts of TEDA in tertiary amine solvent to maintain complete solubility. The weights and compositions of product cuts, and the solubility of TEDA in these tertiary amines at 22° C. are tabulated below in Table I.

TABLE I

| Ex. No. | Amine Solvent | Product Cut Weight, G. | % TEDA | TEDA Solubility % |
|---|---|---|---|---|
| II | 2-dimethylaminoethyl-3-dimethylaminopropy ether | 595 | 19.2 | 10.2 |
| III | dimethylcyclohexylamine | 601 | 23.1 | 12.1 |
| IV | dimethylbenzylamine | 559 | 21.3 | 15.2 |
| V | N-ethylmorpholine | 556 | 24.1 | 16.3 |

Obviously, many modifications and variations of the invention as set forth may be made without departing from the spirit and scope thereof, and therefore, only such limitations should be imposed as are indicated in the appended claims.

We claim:

1. An improved process for directly recovering a substantially pure triethylenediamine solute in a liquid tertiary amine solution from a crude triethylenediamine reaction product mixture obtained from a liquid phase process for the preparation of triethylenediamine comprising the steps of admixing a tertiary amine with said crude triethylenediamine reaction product mixture to form a crude triethylenediamine reaction product-tertiary amine admixture; distilling said admixture under conditions such that said triethylenediamine and said tertiary amine are codistilled; and collecting the resultant codistillate as a substantially pure triethylenediamine solute in liquid tertiary amine solution.

2. The process of claim 1 wherein said collecting of the resultant codistillate is accomplished at a head temperature of from 125° to about 215° C. at atmospheric pressure.

3. The process of claim 2 wherein said tertiary amine is N,N,dimethylethanolamine.

4. The process of claim 1 wherein said crude triethylenediamine reaction product mixture is obtained by heating N-(2-hydroxyethyl)piperazine in the presence of a carboxylic acid catalyst at a temperature ranging from about 230° to about 350° C., and collecting the vaporous effluent therefrom.

5. The process of claim 1 wherein said crude triethylenediamine product is in the wet hexahydrate crystalline form.

* * * * *